BEST AVAILABLE COPY
June 12, 1951 P. M. BOURNE Plant Pat. 1,016
ROSE PLANT
Filed May 19, 1950
Fig. 1.
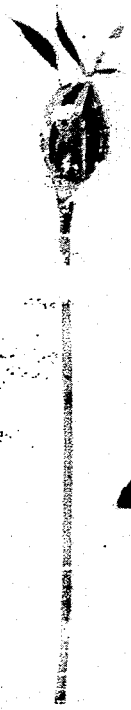
Fig. 2.
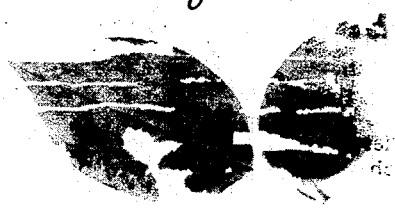
Fig. 3.
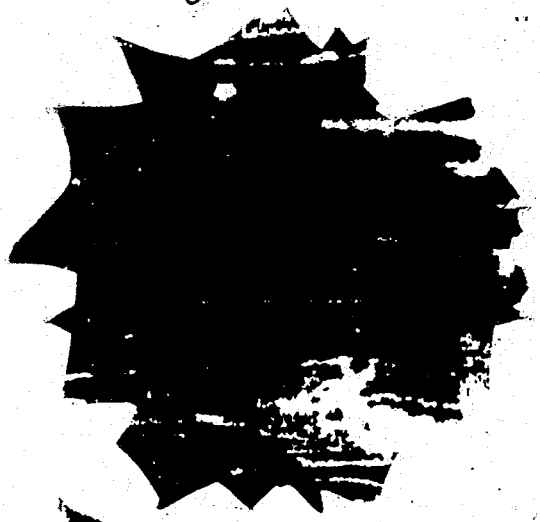
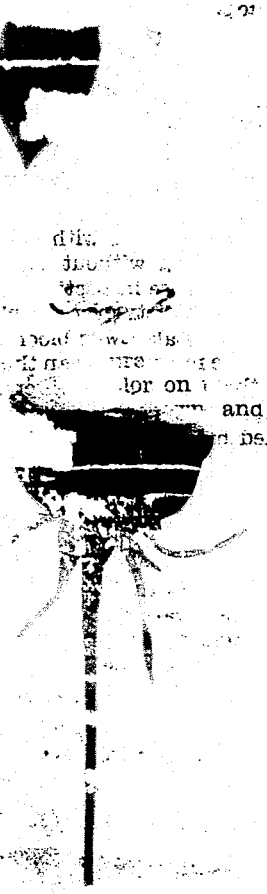
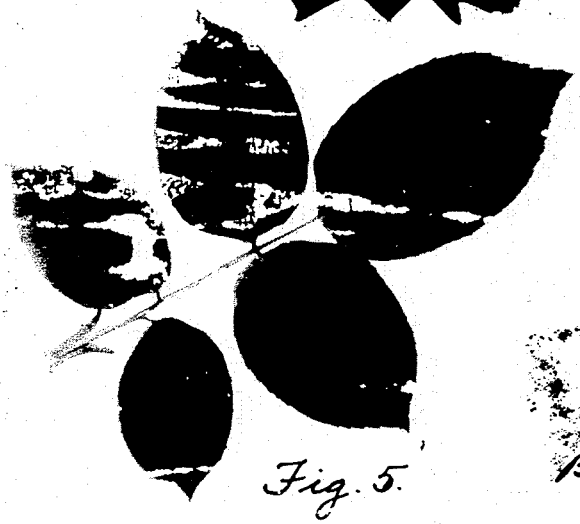
Fig. 5.
Inventor.
P. M. Bourne
By Robb & Robb
Attorneys.

BEST AVAILABLE COPY

Patented June 12, 1951

Plant Pat. 1,016

UNITED STATES PATENT OFFICE 1,0

ROSE PLANT

Percy M. Bourne, Indianapolis, Ind., assignor [illegible] Brothers, Inc., Indianapolis, Ind., a corporation of Indiana Application May 19, 195[illegible] Serial N[illegible] 162,829

1 Claim. ([illegible])

The [illegible] invention relates to a new and distinct va[illegible] rose plant of the hybrid tea class, originati[illegible] a sport of the well-known and [illegible]ty "Be[illegible] Times" [illegible]lant [illegible] No[illegible] produces the ma[illegible]ity of [illegible] red colo[illegible]s g[illegible] flow[illegible]s.

[illegible] attention while [illegible] a "Better Times" plant in the gre[illegible] reason of the fact that despite [illegible] fumigation of the greenhouse plants [illegible] "azobenzene," which [illegible] tends t[illegible]ach the color of the [illegible] of the [illegible]oms of "Better Times," the blooms on the [illegible] shoot showed a marked [illegible]trast [illegible] those [illegible] parent plant [illegible] color of car[illegible]d, with the color [illegible] fa[illegible] or bluing.

[illegible]tion a[illegible]bservation of the [illegible] a prolong[illegible]d period showed [illegible] blooms were more reflexed [illegible] those of "Better Times," [illegible]ed [illegible] color from the [illegible] parent by [illegible]er and acc[illegible]panied by red color o[illegible] [illegible]d midrib.

Despite the foregoi[illegible] teristics, this new variety [illegible] and floriferousness [illegible] "[illegible]imes" parent, thereby representing a [illegible] of color and form of flowe[illegible] of foli[illegible] habit of growth that is [illegible] not [illegible]ly from the parent variety "Better Tim[illegible]" but also distinct from any other [illegible]wn variety.

Asexual reproduction by budding, [illegible]ing and cuttings at Indianapolis, Indiana, shows that the aforementioned [illegible]teristics come true to form and a[illegible]ished and transmitted through succeeding propagations.

In the accompanying drawing—

Fig. 1 shows a specimen bud of the new variety a[illegible] the calyx breaks;

Fig. 2 shows a specimen of a partly open bloom;

Fig. 3 shows a specimen of a full-open flower;

Fig. 4 depicts a specimen of mature foliage with three leaflets, showing under-surface color; and Fig. 5 is a specimen of the mature foliage with five leaflets, showing the upper surfaces.

The following is a detailed des[illegible]ption of the new variety, with color terminol[illegible]y in accordance with Ridgway's Color Standards and Nomenclature, [illegible]cept where otherwise noted in accordance with [illegible]tional general color terms:

Type: Bush; greenhouse; sport; for cut flowers.

Class: Hybrid tea.

Parentage: Sport of "Better Times."

*Flower*

(Observ[illegible]ions m[illegible] in green[illegible] at Indianapolis [illegible] month [illegible]ary, 1950.)

Flowers born [illegible] stron[illegible] [illegible]ems.

Blooming ha[illegible] [illegible] in g[illegible]se, continuous gro[illegible]

[illegible]grance [illegible]rate; pleasing.

[illegible] M[illegible] [illegible]; m[illegible]m green; almost smooth with few prickles.

*Before calyx breaks.*—Medium size; poi[illegible] ovoid; foliaceous parts of calyx extending beyond the tip of the bud [illegible] three-fourths or more of its length. Color—Parrot Green, Plate VI.

*As calyx breaks.*—Exposed petals. Color—Carmine, Plate I, overlaid with Garnet Brown, Plate I.

*As first petal opens.*—Size—medium to large. Form—long; pointed. Color—outside: Satiny Pomegranate Purple, Plate XII, overlaid with Oxblood, Plate I; intensity of color extending to base of petals; inside: Carmine, Plate I, overlaid with Oxblood, Plate I, with distinct velvety sheen.

*Opening.*—Opens [illegible] well with all petals reflexing at margins. Is not affected by adverse weather conditions.

Bloom: Size, when f[illegible]y open—large; measuring from 4¾ inches to 5 inches in diameter.

*Petalage.*—Very [illegible]ouble; with 40 to 55 petals including 5 or [illegible]re petaloid stamens, arranged regularly.

*Form.*—Full; high centered; petals being at first tightly cupped in [illegible]ard; at maturity, loosely rolled outward, except petals at center and petaloi[illegible] which irregular[illegible] cup inward, hiding s[illegible]mens and pistils. All petals, including [illegible]termediate [illegible] ones are reflexed at their margins.

Petals: Thick; inside velvety and outside [illegible]

*Shape.*—Outside — broadly obovate. Intermediate—round. Inner—ovate.

This description of a newly opened flower was made from a rose grown in a greenhouse in the month of February, 1950, at Indianapolis, Indiana:

*Color.—Outside petal*—outside surface: Satiny Pomegranate, Plate XII, overlaid with Oxblood, Plate I, intensity of color extending to base of petal; inside surface: Carmine, Plate I, overlaid with Oxblood, Plate I; velvety texture. *Intermediate petal*—outside surface: Exposed portions same as

BEST AVAILABLE COPY outside petals; toward base becoming lighter through Rose Color, Plate XII, to Deep Rose Pink, Plate XII; inner surface: Exposed portions similar to outside petals. Near base color becomes lighter, similar to outside surface. *Inner petal*—outside surface: Similar to intermediate petals. Inner petals roll inward but reflexed portion of inner surface is the part normally exposed. This part is deep velvety Oxblood, Plate I. Innermost petals or petaloids may have a light stripe extending from base toward margin.

*Color retention.*—Repeated trials in checking mature blossoms kept in storage three days showed no change from above colors. When kept from five to eight days colors became slightly lighter but lacked any of the bluish tinge characteristic of the parent, "Better Times," which were kept under identical conditions.

*Reproductive organs*

Stamens: Arranged regularly about pistils.
Filaments: Medium length; most with anthers. Color—Rose color, Plate XII, to Deep Rose Pink, Plate XII, near anthers.
Anthers: Color—Cinnamon Buff, Plate XXIX.
Pollen: Sparse.
Pistils: Many.
Styles: Uneven; medium length; bunched. Color—Deep Rose Pink, Plate XII, beneath stigma fading to white near ovary.
Stigma: Color—Light Ochraceous Buff, Plate XV.
Ovaries: Some protruding from calyx.
Hips: Short; ovoid; green; smooth.
Sepals: Permanent; moderately long, recurved. Color—inner surface: Asphodel Green, Plate XLI, darkening to Varley's Green, Plate XVIII, at tip; outer surface: Rinnemann's Green, Plate XVIII, at base to Varley's Green, Plate XVIII, at tips. Sometimes overlaid with bronze at margins.

*Plant*

Foliage:
*Leaves.*—Compound of 3, 5 or 7 leaflets; medium large; leathery, glossy.
*Leaflets.*—Oval with apex acute; base round; margin serrate.

*Color.*—*Mature leaf*—upper surface: Dark Dull Yellow Green, Plate XXXII; serrations bronzed at margins on older leaves; under surface: Color ranges between Tea Green, Plate XLVII, and Pea Green, Plate XLVII.
*Rachis.*—Medium heavy. Upper surface: Smooth; groove; under side: With few short prickles except on blooming shoot near peduncle. Color—Pois Green, Plate XLI, overlaid with Vandyke Red, Plate XIII, which often extends into mid-rib on older leaves.
*Stipules.*—Medium length; with medium length points turning out at an angle of about 45°. Color—Pois Green, Plate XLI, overlaid with Vandyke Red, Plate XIII.
*Disease resistance.*—Equal to or greater than parent "Better Times."

Growth:
*Habit.*—Upright; branche[illegible]
*Canes.*—Medium heavy.
*Growth.*—Vigorous.
*Main stems.*—Color—dull green. Few short thorns hooked downward, with long, narrow bases.
*Branches.*—Color—bright green. *Thorns.*—Few short thorns hooked downward, with long, narrow bases. Color—Vinaceous, Plate XXVII. *Prickles and hairs.*—none.

I claim:

A new and distinct variety of rose plant of the Hybrid Tea class, characterized as to novelty and distinguished from its parent by the deeper color of the blooms which are brilliant carmi[illegible] overlaid with oxblood, by [illegible] of the blooms without fad[illegible] greater number of petal[illegible] the petals more reflexed [illegible] inner petals tending to cup in[illegible] stamens and pistils in the ro[illegible] the darker foliage with red co[illegible] and mid-rib, substantially as shown [illegible] described.

PERCY M. BOURNE.

No references cited.